United States Patent [19]

Hayase et al.

[11] Patent Number: 4,720,488

[45] Date of Patent: Jan. 19, 1988

[54] 2-PHENYLIMINO-1,3-THIAZOLIDIN-3-ORGANOPHOSPHORUS COMPOUNDS HAVING PESTICIDAL ACTIVITY

[75] Inventors: Yoshio Hayase, Kameyama; Mitsuhiro Ichinari, Suzuka; Kazuo Kamei, Edogawa; Junji Taguchi, Ichikawa; Katsuaki Oba, Kouka; Toshio Takahashi, Nishinomiya, all of Japan

[73] Assignee: Shionogi & Co., Ltd., Osaka, Japan

[21] Appl. No.: 939,104

[22] Filed: Dec. 8, 1986

[30] Foreign Application Priority Data

Dec. 7, 1985 [JP] Japan .................. 60-275297

[51] Int. Cl.4 .................. A01N 57/24; C07F 9/65
[52] U.S. Cl. ...................... 514/92; 548/111
[58] Field of Search .................. 548/111; 514/92

[56] References Cited

FOREIGN PATENT DOCUMENTS 144794 8/1984 Japan .
144795 8/1984 Japan .
256764 5/1970 U.S.S.R. .

Primary Examiner—Richard L. Raymond
Attorney, Agent, or Firm—Wenderoth, Lind & Ponack

[57] ABSTRACT

A compound of the formula:

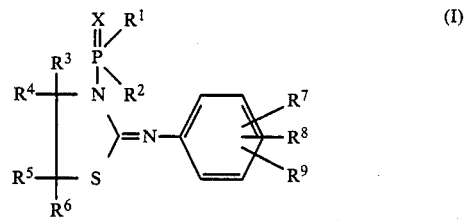

wherein $R^1$ and $R^2$ each represent $C_1$–$C_5$ alkoxy or $C_1$–$C_5$ alkylthio, $R^3$, $R^4$, $R^5$ and $R^6$ each represent hydrogen or $C_1$–$C_5$ alkyl, $R^7$, $R^8$ and $R^9$ each represent hydrogen, $C_1$–$C_5$ alkyl or halogen, and X represents oxygen or sulfur. A process for preparing the compound (I) and a pesticidal composition containing the compound (I) are also provided.

2 Claims, No Drawings

2-PHENYLIMINO-1,3-THIAZOLIDIN-3-ORGANO-PHOSPHORUS COMPOUNDS HAVING PESTICIDAL ACTIVITY

This invention relates to novel organophosphorus compounds having pesticidal activity. More particularly, it relates to novel organophosphorus compounds containing a thiazolidine ring, to their preparation and to pesticidal compositions containing the novel compounds.

Although a wide variety of pesticides have been put to practical use, more efficient and less toxic pesticides have continuously been sought.

The present inventors previously found that a series of phosphonic acids exhibited an excellent pesticidal activity (see British Patent First Publication No. 2,166,442 and Japanese Patent Application No. 170507/1985). During extended study on organophosphorus compounds, it has been found that an organophosphorus compound of the formula:

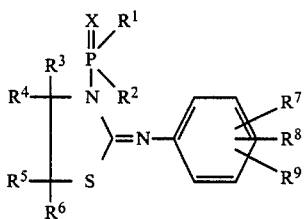

(I)

wherein $R^1$ and $R^2$ each represent $C_1$–$C_5$ alkoxy or $C_1$–$C_5$ alkylthio, $R^3$, $R^4$, $R^5$ and $R^6$ each represent hydrogen or $C_1$–$C_5$ alkyl, $R^7$, $R^8$ and $R^9$ each represent hydrogen, $C_1$–$C_5$ alkyl or halogen, and X represents oxygen or sulfur, exhibits an excellent pesticidal activity on various pests, particularly on spider mites which show resistance to known pesticides. The present invention has been completed on the basis of the above finding.

The term "pests" herein used should be considered to mean both insects and mites harmful to plants, especially phytophagous ones, and, the term "pesticides" or "pesticidal composition" to include insecticides and acaricides.

The compounds of the invention may be prepared according to the following reaction schema:

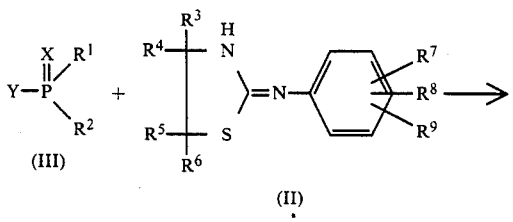

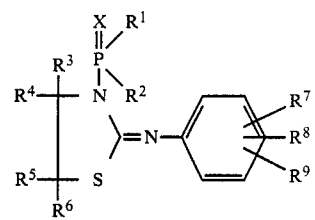

(I)

wherein Y represents a leaving group, $R^1$, $R^2$, $R^3$, $R^4$, $R^5$, $R^6$, $R^7$, $R^8$, $R^9$ and X are as defined above The term "$C_1$–$C_5$ alkyl" herein used refers to a straight or branched saturated hydrocarbon radical having one to five carbon atoms, including methyl, ethyl, propyl, isopropyl, butyl, isobutyl, sec-butyl, tert-butyl, pentyl, isopentyl, tert-pentyl, neopentyl, 1-methylbutyl, 1,2-dimethylpropyl, and the like.

The term "$C_1$–$C_5$ alkoxyl" refers to the $C_1$–$C_5$ alkyl attached to a divalent oxygen atom and includes methoxy, ethoxy, propoxy, isopropoxy, butoxy, pentyloxy, and the like.

The term "$C_1$–$C_5$ alkylthio" refers to the $C_1$–$C_5$ alkyl attached to a divalent sulfur atom and includes methylthio, ethylthio, propylthio, isopropylthio, butylthio, pentylthio, and the like.

The term "halogen" means chloro, bromo, iodo or fluoro.

The term "leaving group" means any group which is readily removed from the moiety to which it has been attached. Such leaving groups are exemplified by chloro, bromo, iodo, or other acid residues.

As previously stated, the compound (I) may be prepared by the reaction between the compound (II) and compound (III). The reaction is preferably conducted in an appropriate inert solvent although the use of solvent is not essential. The appropriate solvents include aliphatic hydrocarbons such as n-hexane and cyclohexane, aromatic hydrocarbons such as benzene, toluene and xylene, ketones such as acetone and methyl isobutyl ketone, ethers such as ethyl ether, tetrahydrofuran and dioxane, and halogenohydrocarbons such as dichloromethane and chlorobenzene. In addition, the reaction is conveniently carried out in the presence of an acid scavenger such as aliphatic tertiary amines (e.g. trimethylamine, triethylamine, tributylamine), aromatic amines (e.g. dimethylaniline, diethylaniline), heterocyclic amines (e.g. pyridine, α-picoline, γ-picoline), and inorganic bases (e.g. sodium carbonate, potassium carbonate).

The reaction temperature is from 0° C. to 100° C., preferably from 20° C. to 80° C. The reaction time is one to twelve hours with preferred time being from two to eight hours.

The reaction product may be isolated and purified by conventional procedures such as extraction, recrystallization, column chromatography, etc.

The starting materials used in the present invention may be prepared according to the following reaction schema:

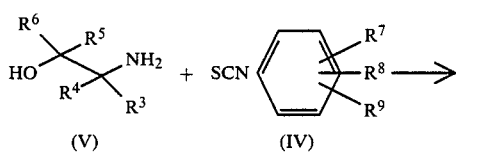

(V)   (IV)

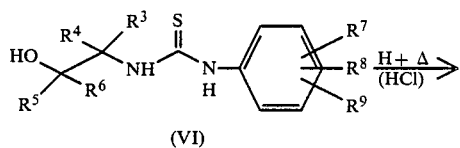

(VI)

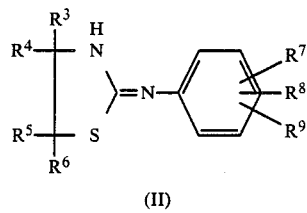

(II)

wherein $R^3$, $R^4$, $R^5$, $R^6$, $R^7$, $R^8$ and $R^9$ are as previously defined.

An aryl isothiocyanate of the formula (IV) is allowed to react with an ethanolamine derivative of the formula (V) to obtain an N-hydroxyethylthiourea compound of the formula (VI), which is then heated at temperature between 100° and 110° C. in the presence of an acid catalyst such as hydrochloric acid to give the aimed starting compound (II). In this reaction, 1.0 to 1.2 mole equivalents of the ethanolamine (V) and 2.0 to 10.0 mole equivalents of the acid catalyst are employed reactive to one mole equivalent of the aryl isothiocyanate (IV).

The compounds of formula (I) of the present invention exhibit an excellent pesticidal activity against phytophagous pests of various orders, such as Acarina, Orthoptera, Heteroptera, Lepidoptera, Diptera and Coleoptera. Therefore, the present invention also provides a pesticidal composition which comprises as an active ingredient a compound of formula (I) together with a suitable carrier and/or adjuvant. The pesticidal composition of the invention may be in any desirable form, such as dusts, granules, wettable powders, emulsifiable concentrates, suspensions, aerosols, flowables, etc., and may be prepared by standard procedures. Solid carriers employable in the preparation of the pesticidal composition of the invention include vegetative flour such as corn, soybean or wheat flour, mineral powder such as clay, bentonite, terra abla, vermiculite, talc, diatomaceous earth, pumice or active carbon, synthetic resins such as vinyl chloride or polystyrene. Illustrative liquid carriers are hydrocarbons such as kerosene, solvent naphtha, toluene and xylenes, alcohols such as methanol, ethanol, ethylene glycol and polypropylene glycol, ethers such as dioxane and cellosolve, ketones such as methyl isobutyl ketone and cyclohexanone, halogenated hydrocarbons such as dichloroethane and trichloroethane, esters such as dioctyl phthalate, amides such as dimethylformamide, nitriles such as acetonitrile, fat and oil, water, and the like.

The adjuvants employed in the preparation of the pesticidal composition of the invention include surfactants, wetting agents, sealing agents, thickening agents, stabilizing agents, etc. Specific examples of the adjuvants are anion surfactants such as alkylsulfonates, lignin sulfonates and alkyl sulfates, nonionic surfactants such as alkylpolyoxyethylene ethers, sorbitan esters, polyoxyethylene fatty acid esters and sucrose esters, water-soluble polymers such as casein, gelatin, carboxymethyl cellulose (CMC), polyvinyl alcohol (PVA), gum arabic and alginic acid.

The composition of the invention may contain, if desired, one or more of other insecticides, bactericides, herbicides, soil conditioners and fertilizers.

The pesticidal composition of the invention contains as an active ingredient about 0.1 to 99.9%, preferably about 2 to 80% by weight of the compound (I). With wettable powder or emulsifiable concentrate, preferred content of the active ingredient ranges from 10 to 50% by weight.

The amount of the composition to be applied to the loci of phytophagous pests will vary depending on a number of factors, such as an application method, season or locus of application, species of pests and crops, and the like. However, the composition is usually applied at the application rate of 200 to 600 liter per 10 are, after diluted to 500 to 10,000 fold, preferably 1,000 to 5,000 fold.

Dust composition of the present invention usually contains from 0.5 to 10%, preferably from 2 to 5% by weight of the compound (I), and are applied at an application rate of from 3 to 10 kg per 10 are.

The following detailed Examples, Formulations and Experiments are presented by way of illustration of certain specific embodiments of the invention.

EXAMPLE 1

2-Phenylimino-1,3-thiazolidin-3-thiolphosphonic acid O-methyl-S-sec-butyl ester (Compound No. 2)

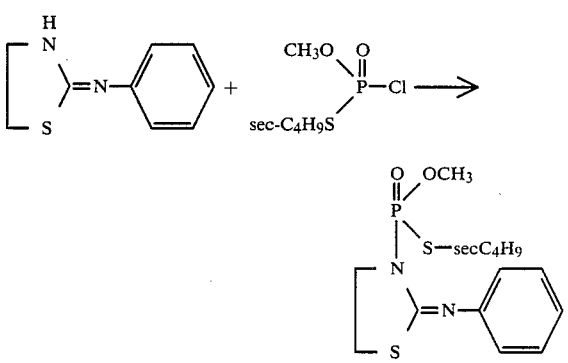

To the mixture of 2-phenylimino-1,3-thiazolidine (2.67 g, 15.0 mM), triethylamine (1.67 g, 16.5 mM) and benzene (30 ml) is dropwise added monochlorothiolphosphoric acid O-methyl-S-sec-butyl ester (3.04 g, 15.0 mM) with stirring at temperature of 10° to 20° C. The mixture is allowed to react at 25° to 30° C. for 3 hours. The resulting triethylamine hydrochloride is filtered off and the benzene layer is successively washed with 3% hydrochloric acid, 3% sodium bicarbonate and water, and concentrated under reduced pressure to give an oil. Yield: 5.12 g.

The oil is purified by column chromatography over silica gel (Wako gel C-300) using n-hexane and acetone (=5:1). Fractions containing the ultimate product are combined and evaporated under reduced pressure to leave transparent colourless liquid. Yield: 3.58 g (69.3%), $n_D^{25} = 1.5833$

EXAMPLE 2

2-(2,6-Dimethylphenyl)imino-1,3-thiazolidin-3-thiol-phosphonic acid O-methyl-S-sec-butyl ester
(Compound No. 4)

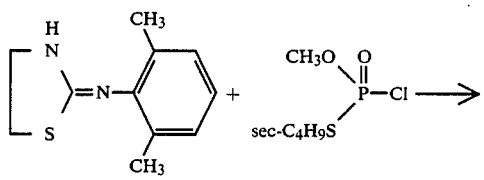

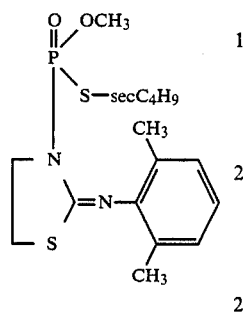

To the mixture of 2-(2,6-dimethylphenyl)imino-1,3-thiazolidine (2.06 g, 10.0 mM), triethylamine (1.11 g, 11.0 mM) and benzene (30 ml) is dropwise added monochlorothiolphosphoric acid O-methyl-S-sec-butyl ester (2.03 g, 10.0 mM) with stirring at 10° to 20° C. The mixture is allowed to react at 25° to 30° C. for 3 hours and the resulting triethylamine is filtered off. The benzene layer is successively washed with 3% hydrochloric acid, 3% sodium bicarbonate and water, and evaporated under reduced pressure to obtain an oil. Yield: 3.67 g.

The oil is purified by column chromatography over silica gel (Wako gel C-300) using n-hexane and acetone (=10:1). The resulting transparent colourless viscous liquid is allowed to cool to yield a white crystal having a melting point of 61.5° to 63.5° C.

EXAMPLE 3

2-(2-Methyl-4-chlorophenyl)imino-1,3-thiazolidin-3-thiolphosphonic acid O-methyl-S-sec-butyl ester
(Compound No. 6)

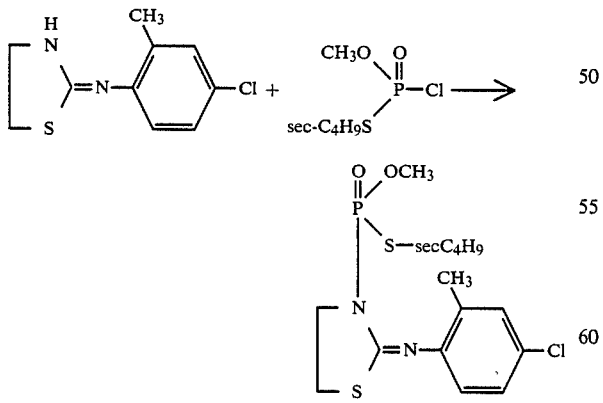

To the mixture of 2-(2-methyl-4-chlorophenyl)imino-1,3-thiazolidine (5.67 g, 25.0 mM), triethylamine (2.78 g, 27.5 mM) and toluene (50 ml) is dropwise added monochlorothiolphosphoric acid O-methyl-S-sec-butyl ester (5.07 g, 25.0 mM) with stirring at 10° to 20° C. The mixture is allowed to react at 25° to 30° C., and the resulting triethylamine hydrochloride is filtered off. The toluene layer is successively washed with 3% hydrochloric acid, 3% sodium bicarbonate and water, and evaporated under reduced pressure to give an oil. Yield: 9.77 g.

The oil is purified as described in Example 2 to give transparent colourless viscous liquid. Cooling of this liquid provides white crystal having a melting point of 60.5° to 62.5° C. Yield: 7.01 g (71.2%).

EXAMPLE 4

2-(2-Methyl-4-chlorophenyl)imino-1,3-thiazolidin-3-thiolphosphonic acid O-ethyl-S-n-propyl ester
(Compound No. 7)

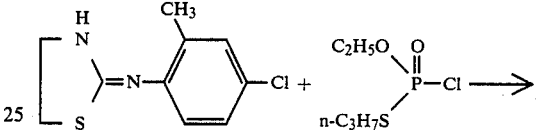

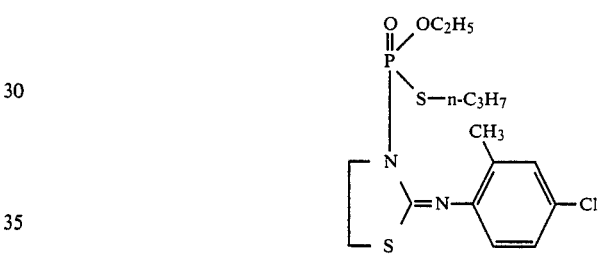

To the mixture of 2-(2-methyl-4-chlorophenyl)imino-1,3-thiazolidine (5.67 g, 25.0 mM), triethylamine (2.78 g, 27.5 mM) and toluene (50 ml) is dropwise added monochlorothiolphosphoric acid O-ethyl-S-n-propyl ester (5.07 g, 25.0 mM) with stirring at 10° to 20° C. The mixture is allowed to react at 25° to 30° C. for 3 hours, and the resulting triethylamine hydrochloride is filtered off. The toluene layer is successively washed with 3% hydrochloric acid, 3% sodium bicarbonate and water, and then evaporated under reduced pressure to give an oil. Yield: 9.64 g.

The oil is purified as described in Example 2 to obtain transparent colourless liquid. Yield: 6.54 g (66.4%), $n_D{}^{25}=1.5817$.

EXAMPLE 5

2-(2,4-Difluorophenyl)imino-1,3-thiazolidin-3-thiolphosphonic acid O-methyl-S-sec-butyl ester
(Compound No. 11)

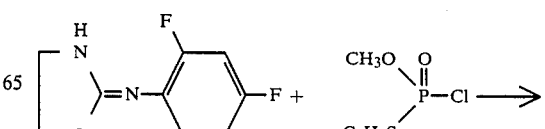

-continued

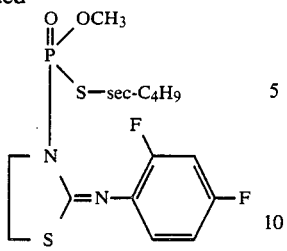
5

To the mixture of 2-(2,4-difluorophenyl)imino-1,3-thiazolidine (1.71 g, 8.0 mM), triethylamine (0.89 g, 8.8 mM) and benzene (30 ml) is dropwise added monochlorothiolphosphoric acid O-methyl-S-sec-butyl ester (1.62 g, 8.0 mM) with stirring at 10° to 20° C. The mixture is allowed to react at 25° to 30° C. for 5 hours, and the resulting triethyl amine hydrochloride is filtered off. The benzene layer is successively washed with 3% hydrochloric acid, 3% sodium bicarbonate and water, and then evaporated under reduced pressure to give an oil. Yield: 3.00 g.

The oil is purified by column chromatography over silica gel (Wako gel C-300) using chloroform and ethyl acetate (=10:1) to provide transparent colourless viscous liquid. Yield: 1.95 g (64.1%), $n_D^{25}$=1.5526.

EXAMPLE 6

2-Phenylimino-5,5-dimethyl-1,3-thiazolidin-3-thiolphosphonic acid O-methyl-S-sec-butyl ester (Compound No. 17)

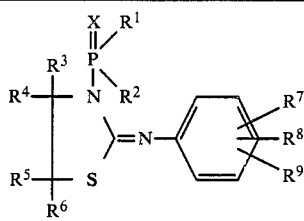

-continued

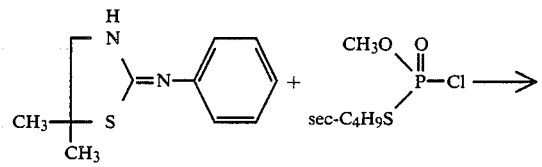

To the mixture of 2-phenylimino-5,5-dimethyl-1,3-thiazolidine (1.65 g, 8.0 mM), triethylamine (0.89 g, 8.8 mM) and benzene (30 ml) is dropwise added monochlorothiolphosphoric acid O-methyl-S-sec-butyl ester (1.62 g, 8.0 mM) with stirring at 10° to 20° C. The mixture is allowed to react at 25° to 30° C. for 3 hours, and the resulting triethylamine hydrochloride is filtered off. The benzene layer is successively washed with 3% hydrochloric acid, 3% sodium bicarbonate and water, and then evaporated under reduced pressure to give an oil. Yield: 2.97 g.

The oil is purified by column chromatography over silica gel (Wako gel C-300) using n-hexane and ethyl acetate (=6:1) to provide transparent colourless viscous liquid. Yield: 1.74 g (58.4%), $n_D^{25}$=1.5634.

EXAMPLE 7-20

In substantial accordance with the procedures as taught in Examples 1 to 6, a variety of compounds (I) of the present invention were prepared. Physico-chemical properties of the compounds are listed in Table 1. NMR and IR data for the compounds listed in Table 1 are summarized in Table 3. In addition, an elementary analysis was conducted for several compounds selected from the compounds listed in Table 1. The results are shown in Table 2.

TABLE 1

(I)

| Compound No. | $R^1$ | $R^2$ | $R^3$ | $R^4$ | $R^5$ | $R^6$ | $R^7$ | $R^8$ | $R^9$ | X | Appearance | m.p. (°C.) | Refractive Index |
|---|---|---|---|---|---|---|---|---|---|---|---|---|---|
| 1 | EtO | n-Pr—S | H | H | H | H | H | H | H | O | transparent colourless liquid | | $n_D^{25}$ 1.5827 |
| 2 | MeO | s-Bu—S | H | H | H | H | H | H | H | O | transparent colourless liquid | | $n_D^{25}$ 1.5833 |
| 3 | EtO | i-Bu—S | H | H | H | H | H | H | H | O | transparent colourless liquid | | $n_D^{25}$ 1.5756 |
| 4 | MeO | sec-Bu—S | H | H | H | H | 2-Me | H | 6-Me | O | white crystal | 61.5–63.5 | |
| 5 | EtO | n-Pr—S | H | H | H | H | 2-Me | H | 6-Me | O | white crystal | 60.0–62.0 | |
| 6 | MeO | s-Bu—S | H | H | H | H | 2-Me | 4-Cl | H | O | white crystal | 60.5–62.5 | |
| 7 | EtO | n-Pr—S | H | H | H | H | 2-Me | 4-Cl | H | O | transparent colourless liquid | | $n_D^{20}$ 1.5817 |
| 8 | EtO | EtO | H | H | H | H | 2-Me | 4-Cl | H | S | transparent colourless liquid | | $n_D^{25}$ 1.5839 |
| 9 | EtO | n-Pr—S | H | H | H | H | 2-Me | 4-Cl | H | S | transparent colourless liquid | | $n_D^{25}$ 1.6078 |
| 10 | EtO | n-Pr—S | Me | Me | H | H | H | H | H | O | transparent colourless liquid | | $n_D^{25}$ 1.5435 |
| 11 | MeO | s-Bu—S | H | H | H | H | 2-F | 4-F | H | O | transparent colour- | | $n_D^{25}$ 1.5526 |

TABLE 1-continued

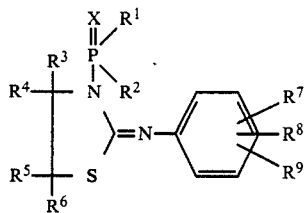
(I)

| Compound No. | R¹ | R² | R³ | R⁴ | R⁵ | R⁶ | R⁷ | R⁸ | R⁹ | X | Appearance | m.p. (°C.) | Refractive Index |
|---|---|---|---|---|---|---|---|---|---|---|---|---|---|
| 12 | EtO | n-Pr—S | H | H | H | H | 2-F | 4-F | H | O | transparent colourless viscous liquid | | $n_D^{25}$ 1.5587 |
| 13 | MeO | s-Bu—S | H | H | Me | Me | H | 4-Cl | H | O | transparent colourless viscous liquid | | $n_D^{25}$ 1.5691 |
| 14 | EtO | n-Pr—S | H | H | Me | Me | H | 4-Cl | H | O | transparent colourless viscous liquid | | $n_D^{25}$ 1.5698 |
| 15 | MeO | s-Bu—S | H | H | Me | Me | 2-Me | 4-Cl | H | O | transparent colourless viscous liquid | | $n_D^{25}$ 1.5645 |
| 16 | EtO | n-Pr—S | H | H | Me | Me | 2-Me | 4-Cl | H | O | transparent colourless viscous liquid | | $n_D^{25}$ 1.5608 |
| 17 | MeO | s-Bu—S | H | H | Me | Me | H | H | H | O | transparent colourless viscous liquid | | $n_D^{25}$ 1.5634 |
| 18 | EtO | n-Pr—S | H | H | Me | Me | H | H | H | O | transparent colourless viscous liquid | | $n_D^{25}$ 1.5637 |
| 19 | MeO | s-Bu—S | Me | Me | H | H | H | H | H | O | transparent yellow liquid | | $n_D^{25}$ 1.5625 |
| 20 | EtO | n-Pr—S | Me | Me | H | H | 2-Et | H | 6-Et | O | white crystal | 102.0–104.0 | |

TABLE 2

| Compound No. | | C | H | N | P |
|---|---|---|---|---|---|
| 1 | Calculated: ($C_{14}H_{21}N_2O_2PS_2$) | 48.82 | 6.15 | 8.13 | |
| | Found: | 48.32 | 6.03 | 7.92 | |
| 2 | Calculated: ($C_{14}H_{21}N_2O_2PS_2$) | 48.82 | 6.15 | 8.13 | |
| | Found: | 48.46 | 6.06 | 8.05 | |
| 7 | Calculated: ($C_{15}H_{22}N_2O_2PS_2Cl$) | 45.85 | 5.64 | 7.13 | |
| | Found: | 45.45 | 5.61 | 7.06 | |
| 6 | Calculated: ($C_{15}H_{22}N_2O_2PS_2Cl$) | 45.85 | 5.64 | 7.13 | 7.88 |
| | Found: | 45.48 | 5.55 | 6.86 | 7.14 |
| 5 | Calculated: ($C_{16}H_{25}N_2O_2PS_2$) | 51.59 | 6.76 | 7.52 | |
| | Found: | 51.95 | 6.95 | 7.39 | |
| 4 | Calculated: ($C_{16}H_{25}N_2O_2PS_2$) | 51.59 | 6.76 | 7.52 | |
| | Found: | 51.02 | 6.62 | 7.10 | |

TABLE 3

| Compound No. | NMR* (ppm) | IR** (cm⁻¹) |
|---|---|---|
| 1 | 1.00(3H,t,J=7.0Hz,CH₃ of —S—nPr), 1.37(3H,t,J=7.0Hz, CH₃ of OEt), 1.66(2H,m,S⌒CH₂⌒), 2.7–3.3(2H,m,SCH₂⌒), 3.20(2H,t,J=6.0Hz,thiazolidine C₅—H), 3.9–4.5(4H,m, CH₂ of OEt,thiazolidine C₄—H), 6.8–7.5(5H,m,aromatic H) | 1240(broad, $-\overset{O}{\underset{\|}{P}}\diagdown$) 1640(C=N—) |
| 2 | 1.00(3H,t,J=7.0Hz,CH₃ of S—secBu), 1.45(3H,dd,J=7.0, 1.0Hz,CH₃ of S—secBu), 3.20(2H,t,J=6.5Hz,thiazolidine C₅—H), 3.4–4.2(3H,m,CH of S—secBu,thiazolidine C₄—H), 3.87(3H,d,J=13.0Hz,OCH₃), 6.8–7.5(5H,m,aromatic H) | 1240(broad, $-\overset{O}{\underset{\|}{P}}\diagdown$) 1640(C=N—) |
| 3 | 1.00(6H,d,J=6.0Hz,CH₃×2 of S—isoBu), 1.38(3H,t,J=7.0Hz, CH₃ of OEt), 1.5–2.0(1H,m,CH of S—isoBu), 2.5–3.3(2H,m, CH₂ of S—isoBu), 3.40(2H,t,J=7.0Hz,thiazolidine C₅—H), 3.9–4.5(4H,m,CH₂ of OEt,thiazolidine C₄—H), 6.8–7.3(5H, m,aromatic H) | 1230(broad, $-\overset{O}{\underset{\|}{P}}\diagdown$) 1640(C=N—) |

TABLE 3-continued

| Compound No. | NMR* (ppm) | IR** (cm$^{-1}$) |
|---|---|---|
| 7 | 1.03(3H,t,J=7.0Hz,CH$_3$ of S—n-Pr), 1.38(3H,t,J=7.0Hz, CH$_2$ of OEt), 1.70(2H,m,S⌒CH$_2$), 2.20(3H,s,φ-CH$_3$), 2.7-3.5(2H,m,SCH$_2$⌒), 3.23(2H,t,J=6.0Hz,thiazolidine C$_5$—H), 3.9-4.5(4H,m,CH$_2$ of OEt,thiazolidine C$_4$—H), 6.6-7.2(3H,m,aromatic H) | 1230(broad, —P(=O)⟨ ) 1640(C=N—) |
| 8 | 1.35(6H,t,J=7.0Hz,CH$_3$ of OEt), 2.17(3H,s,φ-CH$_3$), 3.16 (2H,t,J=7.0Hz,thiazolidine C$_5$—H), 4.0-4.5(6H,m,CH$_2$ of OEt,thiazolidine C$_4$—H), 6.6-7.2(3H,m,aromatic H) | 1635(C=N—) |
| 20 | 1.03(3H,t,J=7.0Hz,CH$_3$ of S—nPr), 1.13 and 1.20(3H×2,t, J=7.0Hz,CH$_3$×2 of φ-Et), 1.38(3H,t,J=7.0Hz,CH$_3$ of OEt), 1.67(2H,m,S⌒CH$_2$), 1.75(6H,d,J=4.0Hz,gem-diCH$_3$ of thiazolidine), 2.50(4H,q,J=7.0Hz,CH$_2$×2 of φ-Et), 2.7-3.2(4H,m,SCH$_2$⌒,thiazolidine C$_5$—H), 4.0-4.5(2H,m,CH$_2$ of OEt), 7.05(3H,s,aromatic H) | 1240(broad, —P(=O)⟨ ) 1620(C=N—) |
| 6 | 1.00(3H,t,J=7.0Hz,CH$_3$ of S—secBu), 1.43(3H,dd,J=7.0 1.0Hz, CH$_3$ of S—secBu), 1.70(2H,m,CH$_2$ of S—secBu), 2.17 (3H,s,φ-CH$_3$), 3.20(2H,t,J=7.0Hz,thiazolidine C$_5$—H), 3.4-4.3(3H,m,CH$_2$ of OEt,thiazolidine C$_5$—H), 3.85(3H,d, J=14.0Hz,OCH$_3$), 6.6-7.2(3H,m,aromatic H) | 1230(broad, —P(=O)) 1640(C=N—) |
| 11 | 1.00(3H,t,J=7.0Hz,CH$_2$ of S—secBu), 1.45(3H,dd,J=7.0, 1.0Hz,CH$_3$ of S—secBu), 1.70(2H,m,CH$_2$ of S—secBu), 3.27 (2H,t,J=7.0Hz,thiazolidine) C$_5$—H), 3.4-4.3(3H,m,CH of S—secBu,thiazolidine C$_4$—H), 3.90(3H,d,J=13.0Hz,OCH$_3$), 6.7-7.2(3H,m,aromatic H) | 1240(broad, —P(=O)⟨ ) 1635(C=N—) |
| 12 | 1.00(3H,t,J=7.0Hz,CH$_3$ of S—nPr), 1.40(3H,t,J=7.0Hz,CH$_3$ of OEt), 1.65(2H,m,S⌒CH$_2$), 2.7-3.5(2H,m,SCH$_2$⌒), 3.27(2H,t,J=7.0Hz,thiazolidine C$_5$—H), 3.9-4.4(4H,m,CH$_2$ of OEt,thiazolidine C$_4$—H), 6.6-7.0(3H,m,aromatic H) | 1240(broad, —P(=O)⟨ ) 1630(C=N—) |
| 4 | 1.03(3H,t,J=7.0Hz,CH$_3$ of S—secBu), 1.45(3H,d,J=7.0Hz, CH$_3$ of S—secBu), 1.70(2H,m,CH$_2$ of S—secBu), 2.16 and 2.20(3H×2,brSφ-CH$_3$×2), 3.20(2H,t,J=7.0Hz,thiazolidine C$_5$—H), 3.4-4.3(3H,m,CH of S—secBu,thiazolidine C$_4$—H), 3.90(3H,d,J=14.0Hz,OCH$_3$), 6.98(3H,s,aromatic H) | 1240(broad, —P(=O)⟨ ) 1640(C=N—) |
| 5 | 1.03(3H,t,J=7.0Hz,CH$_3$ of S—nPr), 1.40(3H,t,J=7.0Hz,CH$_3$ of OEt), 1.70(2H,m,S⌒CH$_2$), 2.15 and 2.20(3H×2,brsφ-CH$_3$×2),2.8-3.3(2H,m,SCH$_2$⌒), 3.20(2H,t,J=7.0Hz,thiazolidine C$_5$—H), 3.9-4.5(4H,m,CH$_2$ of OEt,thiazolidine C$_4$—H), 7.00(3H,s,aromatic H) | 1240(broad, —P(=O)⟨ ) 1640(C=N—) |
| 13 | 1.03(3H,t,J=7.0Hz,CH$_3$ of S—secBu), 1.43(3H,dd,J=7.0, 1.0Hz,CH$_3$ of S—secBu), 1.53(6H,s,thiazolidine gem-diCH$_3$), 1.70(2H,m,CH$_3$ of S—secBu), 3.43(2H,d,J=2.0Hz,thiazolidine C$_4$—H), 3.90(3H,d,J=13.0Hz,OCH$_3$), 7.05(4H,dd,J=24.0, 9.0Hz, aromatic H) | 1240(broad, —P(=O)⟨ ) 1640(C=N—) |

TABLE 3-continued

| Compound No. | NMR* (ppm) | IR** (cm⁻¹) |
|---|---|---|
| 14 | 1.00(3H,d,J=7.0Hz,CH₃ of S—nPr), 1.40(3H,t,J=7.0Hz,CH₃ of OEt), 1.53(6H,s,thiazolidine gem-diCH₃), 1.70(2H,m, S⌒CH₂⌒), 3.03(2H,dt,J=15.0,7.0Hz,SCH₂⌒), 3.85(2H,d, J=2.0Hz,thiazolidine C₄—H), 4.30(2H,m,CH₂ of OEt), 7.06 (4H,dd,J=24.0, 9.0Hz,aromatic H) | 1240(broad, —P(=O)\<), 1630(C=N—) |
| 15 | 1.03(3H,t,J=7.0Hz,CH₃ of S—secBu), 1.45(3H,dd,J=7.0, 1.0Hz,CH₃ of S—secBu), 1.53(6H,s,thiazolidine gem-diCH₃), 1.70(2H,m,CH₂ of S—secBu), 2.20(3H,s,φ-CH₃), 3.4–3.7(1H, m,CH of S—sec-Bu), 3.85(2H,d,J=2.0Hz,thiazolidine C₄—H), 3.86(3H,d,J=13.0Hz,OCH₃), 6.6–7.2(3H,m,aromatic H) | 1240(broad, —P(=O)\<), 1630(C=N—) |
| 16 | 1.00(3H,t,J=7.0Hz,CH₃ of S—nPr), 1.40(3H,t,J=7.0Hz,CH₃ of OEt), 1.53(6H,s,thiazolidine gem-diCH₃), 1.70(2H,m, S⌒CH₂⌒), 2.20(3H,s,φ-CH₃), 3.03(2H,dt,J=15.0,7.0Hz, S—CH₂⌒), 3.87(2H,d,J=2.0Hz,thiazolidine C₄—H), 4.30(2H, m,CH₂ of OEt), 6.6–7.2(3H,m,aromatic H) | 1240(broad, —P(=O)\<), 1630(C=N—) |
| 17 | 1.00(3H,t,J=7.0Hz,CH₃ of S—secBu), 1.43(3H,dd,J=7.0, 1.0Hz,CH₃ of S=secBu), 1.53(6H,s,thiazolidine gem-diCH₃), 1.73(2H,m,CH₂ of S—secBu), 3.4–3.9(1H,m,CH of S—secBu), 3.83(2H,d,J=2.0Hz,thiazolidine C₄—H), 3.88(3H,d,J=13.0Hz, OCH₃), 6.8–7.3(5H,m,aromatic H) | 1240(broad, —P(=O)\<), 1630(C=N—) |
| 18 | 1.00(3H,t,J=7.0Hz,CH₃ of S—nPr), 1.36(3H,t,J=7.0Hz,CH₃ of OEt), 1.50(6H,s,thiazolidine gem-diCH₃), 1.70(2H,m,S⌒CH₂⌒), 3.00(2H,dt,J=15.0,9.0Hz,SCH₂⌒), 3.80(2H,d,J=2.0Hz, thiazolidine C₄—H), 4.30(2H,m,CH₂ of OEt), 6.8–7.3(5H,m, aromatic H) | 1240(broad, —P(=O)\<), 1630(C=N—) |

*Solvent: CHCl₃, Internal Standard: T.M.S.
**Solvent: CHCl₃

The process for preparing the starting compounds employed in the present invention are exemplified below.

PREPARATION 1

2-(2-Methyl-4-chlorophenyl)imino-1,3-thiazolidine (3)

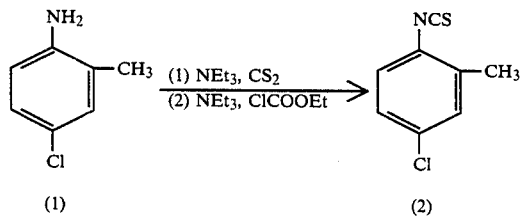

1. 2-Methyl-4-chlorophenyl isothiacyanate (2)

4-Chloro-2-methylaniline (1) (26.1 g) is dissolved in benzene (40 ml). To the solution is added triethylamine (18.6 g). After ice-cooling, carbon disulfide (14.0 g) is dropwise added with stirring over 15 minutes. The reaction mixture is then allowed to warm to room temperature and stirred for 45 minutes. The mixture is allowed to stand overnight in a refrigerator and evaporated to remove the benzene. The residue is dissolved in chloroform (100 ml), and triethylamine (18.6 g) is added to the resulting solution. After addition of ethyl chloroformate (20.0 g) over 10 minutes with stirring and ice-cooling, the reaction mixture is allowed to warm to room temperature, stirred for 3 hours, added with conc. HCl (40 ml) dissolved in water (250 ml), and extracted with chloroform. The chloroform extract is washed with water, dried over Na₂SO₄, and evaporated to remove the solvent. The aimed semi-crystal product (2) is thus obtained as the residue. Yield: 30.3 g (90%). Melting point after purified by silica gel chromatography is 31.5°–32.5° C.

2. 2-(2-Methyl-4-chlorophenyl)imino-1,3-thiazolidine (3)

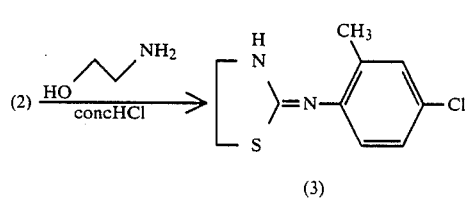

The compound (2) obtained above (12.93 g) is charged in an eggplant type flask (200 ml volume) and 2-aminoethanol (4.32 g) is added thereto. After thorough agitation and heating, the mixture is cooled and conc. HCl (25 ml) is added. The mixture is heated under reflux for 2 hours, cooled, and made basic by addition of 4N NaOH. The precipitated crystal is filtered, washed with water, dried, and recrystallized from methanol. Colourless columnar crystal of the aimed product (3) is thus obtained. m.p.: 137°–139° C. Yield: 9.0 g (57%).

PREPARATION 2

2-(2-Methyl-4-chlorophenyl)imino-5,5-dimethyl-1,3-thiazolidine (4)

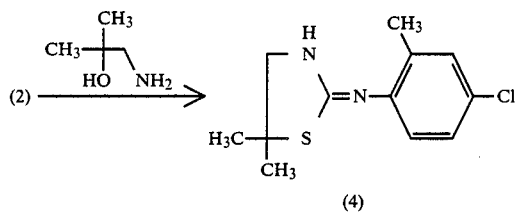

The compound (2) obtained above (5.0 g) is placed in an eggplant type flask (100 ml volume) and (1-amino-2-methyl)-2-propanol (2.43 g) is added thereto. After addition of chloroform (20 ml), the mixture is stirred, evaporated to remove the chloroform, added with conc. HCl (10 ml), refluxed for 40 minutes, cooled, made basic with 4N NaOH, and extracted with chloroform. The chloroform extract is washed with water, dried over Na$_2$SO$_4$, evaporated to remove the chloroform, added with benzene, and filtered to remove insoluble substances. Addition of n-hexane to the filtrate yields the aimed product (4) as a colourless needle. m.p.: 127.5°–130.0° C., Yield: 2.30 g (33%).

| Elementary Analysis (C$_{12}$H$_{15}$N$_2$SCl) | | | |
|---|---|---|---|
| | C | H | N |
| Calculated (%): | 56.57 | 5.93 | 10.99 |
| Found (%): | 56.50 | 5.84 | 10.90 |

PREPARATION 3

2-Phenylimino-5,5-dimethyl-1,3-thiazolidine (6)

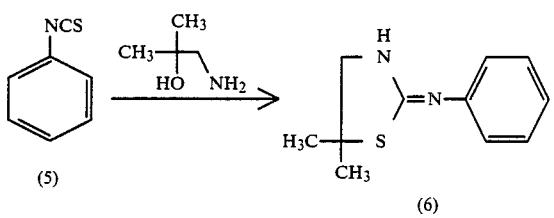

Phenyl isothiacyanate (5) (1.97 g) is placed in an eggplant type flask (50 ml volume) and (1-amino-2-methyl)-2-propanol (1.30 g) is added thereto. The mixture is throughly agitated and heated. After cooling, conc.HCl (15 ml) is added and the mixture is heated under reflux for 3 hours, cooled, and made basic with 4N NaOH. The reaction mixture is extracted with chloroform, and the chloroform extract is washed with water, dried over Na$_2$SO$_4$, evaporated to remove the chloroform, and purified by silica gel chromatography. After recrystallization from methanol, the aimed product (6) having a melting point of 153°–155.0° C. is obtained. Further recrystallization of the product from benzene/n-hexane gives colourless flake having a melting point of 148°–151° C. Yield: 1.7 g (56%).

| Elementary Analysis (C$_{11}$H$_{14}$N$_2$S) | | | |
|---|---|---|---|
| | C | H | N |
| Calculated (%): | 64.04 | 6.48 | 13.58 |
| Found (%): | 63.81 | 6.79 | 13.44 |

PREPARATIONS 4–9

The following starting compounds (II) listed in Table 4 are obtained in the similar manner as described in the foregoing preparations.

TABLE 4

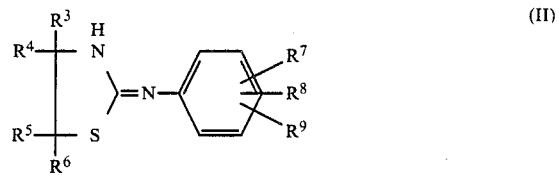

| Preparation No. | R$^3$ | R$^4$ | R$^5$ | R$^6$ | R$^7$ | R$^8$ | R$^9$ | m.p. (°C.) | yield (%) |
|---|---|---|---|---|---|---|---|---|---|
| 1 | H | H | H | H | 2-Me | 4-Cl | H | 137–139 | 57 |
| 2 | H | H | Me | Me | 2-Me | 4-Cl | H | 127.5–130.0 | 33 |
| 3 | H | H | Me | Me | H | H | H | 148–151 | 56 |
| 4 | H | H | H | H | H | H | H | 159–162 | 85 |
| 5 | H | H | H | H | 2-F | 4-F | H | 148–149 | 56 |
| 6 | H | H | H | H | 2-Me | H | 6-Me | 92–93 | 53 |
| 7 | Me | Me | H | H | H | H | H | 158–160 | 48 |
| 8 | Me | Me | H | H | 2-Et | H | 6-Et | 142–144 | 62 |
| 9 | H | H | Me | Me | H | 4-Cl | H | 143.0–146.5 | 30 |

Pesticidal compositions containing as an active ingredient a compound of the invention are illustrated below.

| Formulation 1 Dust | |
|---|---|
| Ingredient | Part by weight |
| Compound No. 1 | 2 |

-continued

| Formulation 1 Dust | |
|---|---|
| Ingredient | Part by weight |
| Clay | 88 |
| Talc | 10 |

The above ingredients are admixed to obtain a dust preparation.

| Formulation 2 Wettable powder | |
|---|---|
| Ingredient | Part by weight |
| Compound No. 3 | 30 |
| Diatomaceous earth | 45 |
| White carbon | 20 |
| Sodium lauryl sulfate | 3 |
| Sodium lignin sulfonate | 2 |

The above ingredients are admixed to obtain a wettable powder preparation.

| Formulation 3 | |
|---|---|
| Ingredient | Part by weight |
| Compound No. 5 | 20 |
| Xylene | 60 |
| Polyoxyethylenephenyl-phenolpolymer | 20 |

The above ingredients are admixed to obtain an emulsifiable concentrate preparation.

Pesticidal activity of the compounds of the invention was determined in accordance with the following procedures.

TEST 1

Samples

The compound (I) of the invention to be tested is dissolved in a minimum amount of DMF. Distilled water containing Tween 20 at the concentration of 100 ppm is thereto added to prepare a series of samples of the desired concentrations.

Test Procedure

A. Suppression of *Spodoptera litura* larvae

Cabbage leaves (7×7 cm) were immersed in the sample solution as prepared above and air dried. Two leaves were placed in a petri dish (9 cm diameter) and 10 second-instar larvae of *Spodoptera litura* were placed in the dish. The dish was held at 25° C. and the mortality of the larvae was determined after 48 hours.

C. Suppression of *Plutella xylostella* larvae

Cabbage leaf (7×7 cm) was immersed in the sample solution and air dried. The leaf was placed in a petri dish (9 cm diameter) and 10 third-instar larvae of *Plutella xylostella* were placed in the dish. The dish was held at 25° C. and the mortality of the larvae was determined after 48 hours.

D. Suppression of *Adoxophyes* sp. larvae

Whole tea leaves were immersed in the sample solution and air dried. Three leaves were placed in a polyethylene petri dish (6 cm diameter, 4 cm depth) and 10 forth-instar larvae of *Adoxophyes* sp. were placed in the dish. The dish was held at 25° C. and the mortality of the larvae was determined after 48 hours.

E. Suppression of *Nephotettix cincticeps* larvae (sensitive strain)

Six or seven rice seedlings of 1.5 to 2 plant age in leaf number were bundled and the foliar parts of the seedlings were sprayed with 2 ml of the sample solution and air dried. The treated seedlings were covered with a transparent plastic cylinder and ten female larvae were placed in the cylinder. The atmosphere in the cylinder was kept at 25° C., and the mortality after 48 hours was determined.

I. Suppression of *Myzus persicae* larvae (sensitive strain)

A polyethylene cup (diameter 6 cm, depth 4 cm) was filled with 0.3% agar gel and a piece of Chinese cabbage leaf (3×3 cm) was placed on the gel. After infesting with second instar larvae on the piece of leaf, 2 ml of the sample solution was sprayed on the cup. The test system was kept at 25° C. for 48 hours and the mortality of the larvae was determined.

J. Suppression of *Myzus persicae* larvae (Resistant)

The same test procedure as above was repeated on *Myzus persicae* resistant.

M. Suppression of *Tetranychus cinnabrinus*

A polyethylene cup (diameter 6 cm, depth 4 cm) was filled with 0.3% agar gel and a piece of kidney bean leaf (diameter 2 cm) was placed on the gel. Twelve adults of *Tetranychus cinnabrinus* were placed on the leaf. After 24 hours at 25° C., dead and feeble worms were removed and 2 ml of the sample solution was sprayed on the cup. Following such treatment the test system was kept at 25° C. and the mortality was determined after 48 hours.

O. Suppression of *Tetranychus urticae*

The same test procedure as above was repeated on *Tetranychus urticae.*

N. Suppression of *Tetranychus cinnabrius* eggs

A polyethylene cup (diameter 6 cm, depth 4 cm) was filled with 0.3% agar gel and a piece of bush bean leaf (diameter 2 cm) was placed on the gel. Seven female adults of *Tetranychus cinnabrius* were placed on the leaf and allowed to egg-deposit while keeping the surrounding atmosphere at 25° C. over 24 hours. After removing the adults, 2 ml of the sample was sprayed on the leaf under a rotary application tower. The test system was kept at 25° C. for 7 days and the mortality of eggs was determined by counting the number of eggs which did not hatch.

P. Suppression of *Tetranychus urticae* eggs

The same test procedure as above was repeated on *Tetranychus urticae* eggs.

T. Suppression of *Henosepilachna vigintioctopunctata* (twenty-eight-spotted beetle) adults Japanese eggplant leaf (6×6 cm) was immersed in the sample solution and air dried. The leaf was placed in a petri dish (9 cm diameter) and 5 adults of *Henosepilachna vigintioctopunctata* were placed in the dish. The dish was held at 25° C. and the mortality was determined after 48 hours.

S. Suppression of *Pophillia japonica* (Japanese beetle) adults

The same test procedure as above was repeated on *Pophillia japonica* adults.

R. Suppression of *Periplaneta americana* larvae

A filter paper soaked with the sample solution was placed in a petri dish (diameter 9 cm). Five *Periplaneta americana* larvae within 7 days after hatching were placed in the dish hold at 25° C. and the mortality after 48 hours was measured.

Table 5 shows the test results in terms of mortality (%) of the worms wherein the following codes are employed.

A: *Spodoptera litura* (larvae)
C: *Plutella xylostella* (larvae)
D: *Adoxophyes sp.I* (larvae)
E: *Nephotettix cincticeps* (larvae)
I: *Myzus persicae* sensitive (larvae)
J: *Myzus persicae* Resistant (larvae)
M: *Tetranychus cinnabrinus* (adult)

-continued

O: *Tetranychus urticae* (adult)
N: *Tetranychus cinnabrinus* (egg)
P: *Tetranychus urticae* (egg)
R: *Periplaneta americana* (larvae)
S: *Pophillia japonica* (adult)
T: *Henosepilachna vigintioctopunctata* (adult)

TABLE 5

| Compound No. | conc. (ppm) | A | C | D | E | I | J | M | N | O | P | R | S | T |
|---|---|---|---|---|---|---|---|---|---|---|---|---|---|---|
| 1 | 1000 | 65 | | | | 58 | | 100 | — | | | 100 | | 100 |
| | 250 | | | | | | | 100 | | 95 | | | 100 | 0 |
| | 63 | | | | | | | 100 | | 35 | | 100 | 95 | 0 |
| | 16 | | | | | | | 55 | | 1 | | 10 | 0 | 0 |
| | 4 | | | | | | | 9 | | | | 0 | | |
| 2 | 1000 | — | | | — | — | | 100 | — | | 100 | | 100 | |
| | 250 | | | | | | | 100 | | 100 | | | 100 | 40 |
| | 63 | | | | | | | 100 | | 89 | | 90 | 94 | 0 |
| | 16 | | | | | | | 100 | | 6 | | 20 | 5 | 0 |
| | 4 | | | | | | | 57 | | | | 0 | | |
| 3 | 1000 | 60 | | | — | 83 | | 100 | — | | | 100 | | 100 |
| | 250 | | | | | | | 100 | | 73 | | | 37 | 100 |
| | 63 | | | | | | | 100 | | 67 | | 100 | 58 | 20 |
| | 16 | | | | | | | 95 | | 11 | | 0 | 42 | 0 |
| | 4 | | | | | | | 20 | | | | 0 | | |
| 7 | 1000 | 100 | | | 7 | 95 | | 100 | 92 | | | 100 | | 100 |
| | 250 | 100 | 70 | 100 | | | | 100 | 94 | 100 | 27 | | | 80 |
| | 63 | 100 | 70 | 90 | | | | 100 | 83 | 100 | 25 | 90 | | 60 |
| | 16 | 45 | 40 | 20 | | | | 100 | 27 | 77 | 2 | 30 | | 0 |
| | 4 | | | | | | | 100 | | | | 0 | | |
| 8 | 1000 | 0 | | | 17 | 28 | | 0 | 79 | | | 100 | | 0 |
| | 63 | | | | | | | | | | | 0 | | |
| | 16 | | | | | | | | | | | 0 | | |
| | 4 | | | | | | | | | | | 0 | | |
| 9 | 1000 | 100 | | | 8 | 0 | | 0 | 11 | | | 100 | | 80 |
| | 250 | 0 | 45 | 10 | | | | | | | | | | |
| | 63 | 0 | 35 | 0 | | | | | | | | 0 | | |
| | 16 | 0 | 5 | 0 | | | | | | | | 0 | | |
| | 4 | | | | | | | | | | | 0 | | |
| 19 | 250 | 0 | | | 0 | 90 | 6 | 100 | 0 | 89 | | 0 | | 0 |
| | 63 | | | | | 10 | 0 | 94 | | 8 | | | | |
| | 16 | | | | | 5 | 0 | 7 | | 0 | | | | |
| | 4 | | | | | | | | | | | | | |
| 20 | 1000 | 100 | | | 0 | 0 | | 100 | 0 | | | 100 | | 100 |
| | 250 | 95 | 65 | 0 | | | | 100 | | 46 | | | | 100 |
| | 63 | 15 | 15 | 10 | | | | 100 | | 23 | | 20 | | 90 |
| | 16 | 0 | 10 | 0 | | | | 83 | | 0 | | 0 | | 20 |
| | 4 | | | | | | | 7 | | | | 0 | | |
| 6 | 1000 | 100 | | | 73 | 100 | | 100 | 77 | | | 100 | | 100 |
| | 250 | 100 | 100 | 100 | 50 | 100 | 19 | 100 | 87 | 100 | 27 | | | 100 |
| | 63 | 100 | 100 | 100 | 6 | 95 | 7 | 100 | 66 | 100 | 17 | 90 | | 40 |
| | 16 | 55 | 70 | 40 | 7 | 18 | 0 | 100 | 38 | 80 | 0 | 0 | | 0 |
| | 4 | | | | | | | 100 | | | | 0 | | |
| 11 | 250 | 40 | 50 | 80 | | 100 | 64 | 100 | 78 | 100 | 54 | | | 100 |
| | 63 | 5 | 25 | 10 | | 11 | 0 | 100 | 74 | 100 | 13 | | | 30 |
| | 16 | 0 | 0 | 5 | | 0 | 6 | 100 | 0 | 28 | 0 | | | 0 |
| | 4 | | | | | | | 51 | | | | | | |
| 12 | 1000 | 100 | | 100 | | 69 | | 100 | 100 | 100 | 100 | | | 100 |
| | 250 | 95 | 10 | 90 | | | | 100 | 99 | 100 | 97 | | | 100 |
| | 63 | 10 | 0 | 35 | | | | 100 | 93 | 100 | 47 | | | 90 |
| | 16 | 0 | | 5 | | | | 100 | 21 | 21 | 1 | | | 10 |
| | 4 | | | | | | | 100 | | | | | | |
| 4 | 1000 | 100 | | | 89 | 100 | | 100 | 100 | | | 100 | | 100 |
| | 250 | 85 | 70 | 100 | | 100 | 29 | | | | | 60 | | 100 |
| | 63 | 35 | 20 | 0 | | 80 | 0 | | | | | 0 | | 80 |
| | 16 | 0 | 5 | 0 | | 3 | 0 | | | | | 0 | | 20 |
| 5 | 1000 | — | | | — | 74 | | 100 | 22 | | | — | | — |
| 13 | 1000 | 100 | | | 100 | 100 | | 100 | | | | 100 | | |
| | 250 | 100 | 100 | 100 | 5 | 100 | 47 | 100 | 100 | 100 | 0 | | | 100 |
| | 63 | 40 | 90 | 75 | 0 | 50 | 0 | 100 | 95 | 100 | 3 | | | 100 |
| | 16 | 0 | 70 | 10 | 8 | 0 | 0 | 100 | 30 | 69 | 0 | | | 50 |
| | 4 | | | | | | | 100 | | | | | | |
| 14 | 1000 | 100 | | | 100 | 100 | | 100 | | | | 100 | | |
| | 250 | 100 | 60 | 100 | 5 | 58 | 0 | 100 | 100 | 100 | 28 | | | 100 |
| | 63 | 15 | 20 | 85 | 0 | 0 | 0 | 100 | 100 | 100 | 12 | | | 100 |
| | 16 | 0 | 0 | 20 | 5 | 0 | 8 | 100 | 70 | 84 | 0 | | | 83 |
| | 4 | | | | | | | 77 | | | | | | |
| 15 | 1000 | 100 | | | 100 | 100 | | 100 | | | | 100 | | |
| | 250 | 100 | 100 | 100 | 4 | 100 | 4 | 100 | 100 | 100 | 11 | | | 100 |

TABLE 5-continued

| Compound No. | conc. (ppm) | A | C | D | E | I | J | M | N | O | P | R | S | T |
|---|---|---|---|---|---|---|---|---|---|---|---|---|---|---|
|  | 63 | 70 | 20 | 75 | 0 | 41 | 0 | 100 | 85 | 100 | 4 |  |  | 100 |
|  | 16 | 0 | 20 | 20 | 0 | 0 | 0 | 100 | 7 | 86 | 3 |  |  | 33 |
|  | 4 |  |  |  |  |  |  | 100 |  |  |  |  |  |  |
| 16 | 1000 | 100 |  |  | 100 | 100 |  | 100 |  |  |  | 100 |  |  |
|  | 250 | 100 | 70 | 85 | 0 | 20 | 0 | 100 | 100 | 100 | 10 |  |  | 100 |
|  | 63 | 75 | 50 | 15 | 0 | 0 | 0 | 100 | 69 | 100 | 3 |  |  | 100 |
|  | 16 | 15 | 20 | 5 | 0 | 0 | 0 | 100 | 0 | 93 | 0 |  |  | 67 |
|  | 4 |  |  |  |  |  |  | 91 |  |  |  |  |  |  |
| 17 | 1000 | 100 |  |  | 100 | 100 | 69 | 100 |  |  |  | 100 |  |  |
|  | 250 | 95 | 100 | 95 | 0 | 100 | 17 | 100 | 83 | 100 | 1 |  |  | 100 |
|  | 63 | 20 | 100 | 0 | 9 | 43 | 0 | 100 | 22 | 100 | 5 |  |  | 17 |
|  | 16 | 5 | 30 | 0 | 0 | 0 |  | 100 | 0 | 36 | 0 |  |  | 0 |
|  | 4 |  |  |  |  |  |  | 100 | 0 |  |  |  |  |  |
| 18 | 1000 | 100 |  |  | 100 | 100 |  | 100 |  |  |  | 100 |  |  |
|  | 250 | 75 | 40 | 35 | 0 | 36 | 0 | 100 | 95 | 100 | 9 |  |  | 83 |
|  | 63 | 5 | 30 | 5 | 0 | 0 | 0 | 100 | 45 | 97 | 1 |  |  | 33 |
|  | 16 | 0 | 0 | 0 | 8 | 0 | 0 | 100 | 0 | 19 | 0 |  |  | 0 |
|  | 4 |  |  |  |  |  |  | 44 |  |  |  |  |  |  |

TEST 2

The acaricidal activity of the compounds (I) was determined using *Pentamerismus oregonensis* which had been collected in the open air and subcultured on a rabbit (40 days-old after molting).

A piece of filter paper was placed on a petri dish (9 cm diameter), and 20 *Pentamerismus oregonenis* were left thereon. Two milliliter of the sample solution adjusted so as to contain 0.1% by weight of Compound No. 6 was sprayed over the mites. The similar procedure was repeated using distilled water, which served as a control.

After 24 and 48 hours, mortality of the mites was determined and compared with that of the control. The death of the mites was recognized by no action against $CO_2$ gas and physical stimulation. The test results are shown in Table 6.

TABLE 6

| Concentration (ppm) | Number of mites | Number of dead mites 24 hrs. | Number of dead mites 48 hrs. | Mortality (%) |
|---|---|---|---|---|
| 1,000 | 20 | 20 | — | 100 |
| 500 | 20 | 19 | 1 | 100 |
| 250 | 20 | 18 | 2 | 100 |
| 125 | 20 | 19 | 0 | 95 |
| control | 20 | 0 | 0 | 0 |

What is claimed is:

1. A compound of the formula:

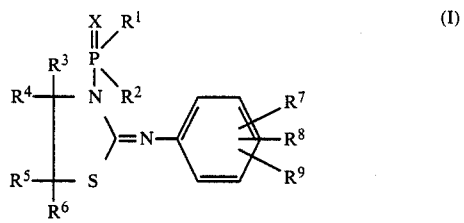

wherein $R^1$ and $R^2$ each represent $C_1$–$C_5$ alkoxy or $C_1$–$C_5$ alkylthio, $R^3$, $R^4$, $R^5$ and $R^6$ each represent hydrogen or $C_1$–$C_5$ alkyl, $R^7$, $R^8$ and $R^9$ each represent hydrogen, $C_1$–$C_5$ alkyl or halogen, and X represents oxygen or sulfur.

2. A pesticidal composition which comprises as an essential component the compound of the formula (I) as defined in claim 1 together with a suitable carrier or adjuvant.

* * * * *